United States Patent [19]
Updike

[11] 3,996,141
[45] Dec. 7, 1976

[54] DIALYSIS MEMBRANE

[75] Inventor: Stuart J. Updike, Madison, Wis.

[73] Assignee: Wisconsin Alumni Research Foundation, Madison, Wis.

[22] Filed: Jan. 17, 1974

[21] Appl. No.: 434,231

Related U.S. Application Data

[63] Continuation-in-part of Ser. No. 191,720, Oct. 22, 1971, Pat. No. 3,846,236.

[52] U.S. Cl. .............................. 210/501; 427/245
[51] Int. Cl.$^2$ ..................................... B01D 13/04
[58] Field of Search .............. 210/22, 23, 321, 500, 210/501, 502; 23/258.5; 195/1.8, 63; 106/194; 264/41, 49; 427/245

[56] References Cited
UNITED STATES PATENTS

| | | | |
|---|---|---|---|
| 2,008,131 | 7/1935 | Dieck et al. | 210/501 X |
| 2,283,883 | 5/1942 | Conconi et al. | 210/501 |
| 2,971,850 | 2/1961 | Barton | 195/63 X |
| 3,158,532 | 11/1964 | Pall et al. | 210/503 X |
| 3,282,702 | 11/1966 | Schreiner | 195/63 X |
| 3,327,859 | 6/1967 | Pall | 210/266 |
| 3,526,481 | 9/1970 | Rubricius | 210/321 X |
| 3,766,013 | 10/1973 | Forgione et al. | 195/63 |
| 3,809,613 | 5/1974 | Vieth et al. | 195/68 X |
| 3,824,150 | 7/1974 | Lilly et al. | 195/DIG. 11 X |
| 3,846,236 | 11/1974 | Updike | 23/258.5 X |

*Primary Examiner*—Frank A. Spear, Jr.
*Attorney, Agent, or Firm*—McDougall, Hersh & Scott

[57] ABSTRACT

A semi-permeable membrane containing a catalyst for conversion of hydrogen peroxide introduced from one side of the semi-permeable membrane to molecular oxygen which is released from the opposite side of the semi-permeable membrane. The catalyst is preferably in the form of a ruthenium oxide or sulfide and preferably in assymetrical distribution in the membrane.

11 Claims, No Drawings

DIALYSIS MEMBRANE

The invention described herein was made in the course of work under a grant or award from the Department of Health, Education, and Welfare. A continuation-in-part application of my copending application Ser. No. 191,720, filed Oct. 22, 1971, and entitled "METHOD AND APPARATUS FOR DIALYSIS", now U.S. Pat. No. 3,846,236.

This application relates to the supply of oxygen to the blood, or other body or chemical fluid, from hydrogen peroxide via a dialysis membrane, and relates more particularly to a catalyst containing dialysis membrane for use in same.

In the aforementioned parent application, description is made of a method and apparatus for the supply of oxygen by conversion of hydrogen peroxide during passage through a semipermeable membrane from a dilute solution of hydrogen on one side of the membrane to a fluid on the opposite side of the membrane. Since the invention has primary application to the supply of oxygen to the blood, bypassed from the human system, at rates sufficient to maintain life, the invention will be described with reference thereto, but it will be understood, as described in the aforementioned application, that the concepts find use in other procedures wherein it is desired to make molecular oxygen available at controlled rates and in amounts suitable for use in other medical applications or chemical operations, such as in various oxygenation or oxygen chlorination processes.

Attempts have previously been made to diffuse molecular oxygen directly through a semipermeable membrane for passage into an extra-corporeal bypassed stream of human blood in contact with the opposite side of the dialysis membrane. This technique has not found acceptance because the rate of diffusion of molecular oxygen through a wettable semipermeable membrane is so slow as to require a diffusion area so large as to make it impractical for use in a respiratory device.

Considerable effort has been expended in another direction of approach, addressed to the supply of oxygen by direct introduction of hydrogen peroxide into the blood-stream, preferably in controlled amounts, as by diffusion through a semipermeable or dialysis membrane, as described in the Rubricius U.S. Pat. No. 3,526,481. In this approach, reliance is had upon the enzyme catalase in the blood to convert the hydrogen peroxide into molecular oxygen and water. This procedure utilizes the catalase activity normally in the blood, and which can be supplemented by injection of highly purified exogenous catalase to break down hydrogen peroxide. However, this technique has been rejected because the conversion rate in the blood plasma is so rapid as to generate oxygen gas bubbles which embolize and can fatally plug the micro-circulation of the lung.

It has been found, in accordance with the invention described in the aforementioned application, that hydrogen peroxide, in dilute solution, can be used to make molecular oxygen available at a rate sufficient to supply venous blood with its requirement to sustain life, when use is made of a dialysis membrane which contains a catalyst for conversion of the hydrogen peroxide to molecular oxygen during diffusion from dilute solution on one side of the wettable membrane to make molecular oxygen available to the blood on the opposite side of the membrane.

Conversion of hydrogen peroxide to molecular oxygen and water occurs in accordance with the following equation:

$$2H_2O_2 \rightarrow O_2 + 2H_2O$$

Thus 2 millimoles of hydrogen peroxide convert to 1 millimole of molecular oxygen. Actual measurement of the amount of oxygen released from a 0.5% solution of hydrogen peroxide on the opposite side of permeable membrane containing $MnO_2$, as a conversion catalyst, was 260 to 450 milliliters per minute per square meter. This is sufficient to provide the basal oxygen requirement for a man of ordinary weight and with a membrane of reasonable dimension for practical use in a respiratory device.

The oxygen converted from dilute hydrogen peroxide solution via a catalyst containing a semipermeable membrane, is made available uniformly over substantially the entire area of the semipermeable membrane for release at a rate sufficient to meet basal oxygen requirements, but without making oxygen available at such high concentrations at any one point as would raise problems of oxygen bubble embolism toxicity.

As the semipermeable membrane, use can be made of a water insoluble, water wettable cellulose derivative, such as cellophane, cellulose acetate, cellulose propionate, carboxyethyl cellulose, and the like; insolubilized gelatin; partially hydrolized polyvinyl acetate; polyionic film forming compositions such as polysulfonated anionic polymers or ionically linked polycationic polymers, such as marketed by Amicon Company. Use can also be made of dialysis membranes formed of multiple hollow fibers, such as marketed by the Dow Chemical Company, or hydrophobic membranes, such as formed of organosilicon rubbers.

In the practice of the invention, it is important to make use of a conversion catalyst that does not wash out of the membrane under acid, neutral, or alkaline conditions so that the semipermeable membrane will remain effective over long periods of continuous use under the widely varying conditions to which it is exposed in dialysis. Another characteristic of the catalyst, in order to achieve the desired utility, over long periods of use, is the freedom of the catalyst from poisoning by components present in the fluids to which it is exposed, or which in turn does not contribute any undesirable components into the bloodstream.

Another factor, which should be taken into consideration, in defining a catalyst containing permeable membrane, suitable for use in the practice of this invention, is the ability to effect substantially complete conversion of the hydrogen peroxide before passage through the semipermeable membrane so that practically no hydrogen peroxide will break through the membrane and be introduced into the bloodstream.

These characteristics are generally derived from the use of an inorganic catalyst. Manganese dioxide has been described in the aforementioned parent application as a preferred catalyst which can be incorporated into the dialysis membrane in accordance with the following example:

EXAMPLE I

An untreated cellophane membrane, of the type previously described as being used in artificial kidney dialysis, is first hydrated in water and then simultaneously exposed on one side to a 0.3 molar potassium permanganate solution, and on the opposite side, to a 0.1 molar sodium iodide solution for one minute. Diffusion of the two solutions from opposite sides into the membrane brings about the precipitation of manganese dioxide in the interior of the dialysis membrane. This gives the membrane a homogeneous translucent amber pigmentation. Instead of making use of sodium iodide for precipitation of $MnO_2$ from the permanganate, other alkali metal iodides or similar reducing agents can be employed. Similarly, other water soluble permanganates, such as sodium permanganate, ammonium permanganate, and the like can be used instead of potassium permanganate. For good diffusion at a uniform rate, it is desirable to make use of a dialysis membrane, in the form of a semipermeable membrane formed of materials that are wet by the fluids disposed on both sides of the membrane. Thus, for use of $H_2O_2$ in aqueous solution on one side and blood plasma on the other, it is preferred to make use of a membrane of hydrophilic material for ready wet-out and absorption of the aqueous medium.

Instead of manganese dioxide, other catalytic agents which may be employed are silver particles, such as colloidal silver and the like formed in situ in the membrane, as by wetting one side of the membrane with a silver nitrate solution while the other side is wet with an alkaline zinc solution for reaction to precipitate silver in fine particle form in the membrane. Similarly, one side of the membrane can be wet with a silver halide solution while the opposite side is wet with a photographic type reducing agent, such as a hyposulfite, for reaction in the interior of the membrane to precipitate silver particles which catalyze the reaction to convert $H_2O_2$ to oxygen and water during transport therethrough. Colloidal and chelated iron and the more noble metals platinum and gold can also be used.

Catalysts for conversion of $H_2O_2$ to oxygen are well known to include such metals as platinum, silver and gold, from which suitable porous membranes can be formed. Porous metal membranes can be constructed by pressure and/or heat sintering of the materials, or by a photographic etching technique, and are available commercially at a thickness of 3 microns and at a pore size of 0.2 micron. These membranes can then be used to support a cellulose or silicone rubber film polymerized over the surface of the metal.

Suitable, though less desirable from the standpoint of efficiency and wash-out, are such organic catalysts as the enzyme catalase iron-albumin mixtures, colloidal cholesterol and some organic compounds of nonbiologic origin, such as phthalocyamines.

Description will hereinafter be made of a catalyst system which has been found to be uniquely suitable for use with dialysis membranes in a respiratory device. It has been found that when ruthenium is incorporated as the sulfide or oxide as a catalyst in a semipermeable membrane, the catalyst resists leaching or wash-out under acid, neutral or alkaline conditions. It is not easily poisoned by components to which it is exposed during respiratory dialysis and it effectively prevents breakthrough of hydrogen peroxide by remaining active to effect substantially complete conversion of the hydrogen peroxide to oxygen for passage through the semipermeable membrane.

EXAMPLE II

An untreated cellophane membrane of the type described in Example I is first hydrated in water and then simultaneously exposed on one side to a 0.25 M. solution of ruthenium chloride (103) and on the opposite side to a 0.1 M. sodium hydroxide solution. Diffusion of the two solutions from opposite sides to the membrane brings about precipitation within the membrane of ruthenium oxide or its hydrated form. The solutions are then rinsed from the membrane, leaving the membrane with its insoluble precipitate of ruthenium oxide substantially uniformly distributed therethrough.

EXAMPLE III

The procedure of Example II is followed but instead of sodium hydroxide solution, the membrane is exposed to a solution of sodium sulfide whereby the precipitate that is formed in situ in the membrane is ruthenium sulfide or its hydrated form.

The resulting catalyst containing membranes of Examples II and III have been subjected to a number of tests including wash-out and poisoning.

The catalyst contained membranes were soaked for 48 hours in whole blood, blood plasma, hepernized whole blood, aqueous solutions containing carbonate, arsenate, phosphate and chloride ions, without any noticeable poisoning of the catalyst as measured by its subsequent catalyst activity for conversion of hydrogen peroxide to molecular oxygen.

The catalyst containing membrane was tested for wash-out or leaching by soaking over an extended period of time in aqueous alkaline, acid or neutral solutions, in EDTA and boiling EDTA, without any deterioration in the catalyst due to leaching. There is reason to believe that the ruthenium ion forms a unique covalent bond with hydroxyl groupings present in the membrane which resists removal by washing or leaching.

When, as described in Examples II and III, the dialysis membrane is exposed simultaneously to a solution of a soluble ruthenium salt on one side and the sodium hydroxide or other alkaline solution on the other side, the ruthenium oxide precipitates rather uniformly throughout the membrane to form what may be described as a symmetrical membrane.

It has been found advantageous to provide an asymmetrical membrane wherein the catalyst such as ruthenium oxide or sulfide is present in higher concentrations on one side to enable the side with the higher concentration of catalyst to be positioned to be wet by the bloodstream in the respiratory device. Such asymmetrical membranes can be obtained in a number of ways: the membrane can be soaked in a solution of sodium hydroxide or other soluble alkali for a time uniformly to penetrate the membrane. After rinsing off the excess alkaline solution, one side of the impregnated membrane is exposed to the solution of the ruthenium salt, such as a 0.5% solution of ruthenium chloride. Ruthenium oxide will precipitate progressively from the side wet with the ruthenium salt. Thus a membrane can be formed in which the catalyst concentration tapers off from a maximum on one side to a point which is substantially free of catalyst, preferably short of the other side.

The same effect can be obtained by impregnation or incorporation of the ruthenium salt first in the membrane for uniform distribution therein, followed by exposing one side to the alkaline solution or the sulfide solution to cause precipitation of the corresponding ruthenium oxide or sulfide in concentrations which diminish gradually from the side contacted with the sulfide or alkaline solution.

Such asymmetrical dialysis membrane, arranged in the respiratory device with the side having the higher concentration of catalyst in contact with the bloodstream, provides more effective insurance against breakthrough of hydrogen peroxide. During diffusion through the membrane, the decreasing concentration of hydrogen peroxide comes into contact with increasing concentration of catalyst, whereby the last traces of hydrogen peroxide are readily converted to molecular oxygen before reaching the opposite or blood contacting side of the membrane.

While the asymmetrical arrangement has been described with reference to the preparation of membranes with a catalyst of ruthenium oxide or sulfide, it will be apparent that such asymmetrical arrangements can be achieved with others of the inorganic or organic catalyst described.

Instead of providing the asymmetrical arrangement by precipitation of the catalyst in situ in the dialysis membrane, the desired arrangement can otherwise be achieved. For example, thin films of membrane material having different concentrations of catalysts provided therein, can be preformed and then laminated in a desired arrangement to form a composite dialysis membrane having different concentrations of catalysts in cross section calculated for optimum results. Such catalyst can be provided in the desired concentrations in the films by separate precipitation from solutions of different concentration, or by introduction of the catalyst as a particulate material into the material of which the film or membrane is subsequently formed.

The dialysis membrane of this invention may be used in the manner described in the parent application, Ser. No. 191,720, for oxygenation of venous blood by arrangement in a dialysis apparatus with a 0.5% by weight $H_2O_2$ solution in water in position to wet one side of the membrane while venous blood is bypassed from the human system into the dialysis device in position to wet the opposite side of the membrane. Upon diffusion of hydrogen peroxide into the membrane, the hydrogen peroxide is converted to molecular oxygen which is made available from the opposite side of the membrane for introduction into the blood as a respiratory device.

It will be understood that changes may be made in the details of construction, arrangement and operation without departing from the spirit of the invention, especially as defined in the following claims.

I claim:
1. A dialysis membrane formed of a high molecular weight film forming material as a continuous phase containing within the membrane an insoluble inorganic catalyst which does not wash out of the membrane and which converts hydrogen peroxide in dilute solution to water and oxygen during passage of the dilute solution of hydrogen peroxide thereinto from one side for release of oxygen from the opposite side in which the catalyst is selected from the group consisting of manganese dioxide, ruthenium oxide, ruthenium sulfide, colloidal silver, colloidal and chelated iron, platinum, silver and gold.

2. A membrane as claimed in claim 1 in which the catalyst distribution in the membrane is asymmetrical.

3. A membrane as claimed in claim 1 in which the catalyst concentration is greater adjacent one side of the membrane than the other.

4. A method of producing a dialysis membrane formed of a high molecular weight film forming material as a continuous phase containing within the membrane an insoluble catalyst in the form of a metal oxide or sulfide which converts hydrogen peroxide from dilute solution to water and molecular oxygen during diffusion of hydrogen peroxide from one side for release of oxygen from the opposite side comprising incorporating one of the components including a soluble salt of the metal and a soluble sulfide or hydroxide in the membrane and then wetting the membrane with a solution of the other component for reaction with the first component in situ in the membrane to precipitate the corresponding metal oxide or sulfide.

5. The method as claimed in claim 4 in which the one component is incorporated by contacting the membrane with a solution of the one component for diffusion into the membrane, and then contacting the membrane with a solution of the other component.

6. The method as claimed in claim 4 in which a membrane is produced with an asymmetrical catalyst comprising wetting one side of the membrane with a solution of one component while wetting the opposite side of the membrane with a solution of the other component.

7. The method as claimed in claim 4 in which a membrane is produced with an asymmetrical catalyst comprising wetting the membrane with a solution of one component for introducing the component in uniform distribution in the membrane, and then wetting one side of the membrane with a solution of the other component whereby precipitation of the metal oxide or sulfide commences at the side wet with the other component.

8. The method of producing a membrane as claimed in claim 4 in which the catalyst is ruthenium oxide or sulfide comprising the steps of wetting one side of the membrane with an aqueous solution of a water soluble salt of ruthenium and wetting the opposite side of the membrane with an alkali metal sulfide or hydroxide.

9. The method as claimed in claim 8 in which the ruthenium salt is ruthenium trichloride.

10. The method of producing a membrane as claimed in claim 4 with the catalyst in asymmetrical distribution in the membrane comprising wetting the membrane first with a solution of a soluble salt or ruthenium for substantially uniform distribution of the ruthenium salt in the membrane, and then wetting the one side from which the oxygen is to be released with a soluble sulfide or hydroxide to begin precipitation of the corresponding ruthenium oxide or sulfide from the one side.

11. The method of producing a membrane as claimed in claim 4 with the catalyst in asymmetrical distribution in the membrane comprising wetting the membrane first with a solution of a soluble sulfide or hydroxide for substantially uniform distribution of the sulfide or hydroxide in the membrane, and then wetting the one side from which the oxygen is to be released with a solution of a soluble salt of ruthenium to cause precipitation to begin at the one side.

* * * * *